United States Patent [19]

Mathys

[11] Patent Number: 4,476,341

[45] Date of Patent: Oct. 9, 1984

[54] BUTENE DIMERIZATION METHOD

[75] Inventor: Georges M. K. Mathys, Bierbeek, Belgium

[73] Assignee: Exxon Research & Engineering Co., Florham Park, N.J.

[21] Appl. No.: 480,257

[22] Filed: Mar. 30, 1983

[30] Foreign Application Priority Data

Apr. 6, 1982 [GB] United Kingdom ............... 8210236

[51] Int. Cl.$^3$ .............................................. C07C 2/24
[52] U.S. Cl. ..................................... 585/512; 585/513
[58] Field of Search ................................ 585/512, 513

[56] References Cited

U.S. PATENT DOCUMENTS

| | | | |
|---|---|---|---|
| 3,321,546 | 5/1967 | Roest et al. | 260/683.15 |
| 3,655,810 | 4/1972 | Chauvin et al. | 260/683.15 D |
| 3,658,935 | 4/1972 | Pine et al. | 260/683.15 R |

OTHER PUBLICATIONS

V. Sh. Fel'dblyum et al., Neftekhimya, 7, pp. 379–389, (1967), English translation.

*Primary Examiner*—Curtis R. Davis
*Attorney, Agent, or Firm*—Rebecca Yablonsky

[57] ABSTRACT n-Butene is dimerized with improved conversion using an in situ produced homogeneous catalyst system formed from a nickel compound such as nickel octoate, an organoaluminium compound such as aluminium monoethyl dichloride, the butene and hydrogen.

16 Claims, No Drawings

BUTENE DIMERIZATION METHOD

This invention relates to a method of dimerising n-butenes using a homogeneous liquid phase catalyst.

The homogeneous oligomerisation of light olefins such as ethylene, propylene and butene is well known and is described for example in U.S. Pat. No. 3,321,546, in accordance with which the oligomerisation reaction is catalysed by a nickel complex activated by an organo aluminium halide compound. The active catalyst is believed to be a complex entity formed in situ by contact between the olefin, the nickel complex and the aluminium compound. This oligomerisation reaction is performed at a temperature of from $-20°$ to $+40°$ C., which is appropriate for the oligomerisation and also for formation of the active three component catalyst system.

Four component in situ formed catalyst systems have been proposed for use in oligomerisation methods: thus in accordance with U.S. Pat. No. 3,655,810, as fourth component there is added a trace amount of water, and in accordance with European patent application no. 0012685 there is added a small quantity of a Bronstedt acid. Both of such systems are said to give an increased conversion to the oligomer. V. Sh. Fel'dbylum et al in Neftekhimya, 7, pp 379 to 389 (1967), English translation, describe a catalyst system for the dimerisation of propylene which comprises diisobutyl aluminum chloride and nickel oleate in tertiary butyl toluene, and which is said to give up to 97% of dimer. Cetain imputities such as butadiene are said to inhibit the reaction, whereas others such as oxygen or hydrogen are said to increase the catalyst activity. In accordance with U.S. Pat. No. 3,658,935 hydrogen is deliberately introduced into a feed stream of butene and/or propylene which contains acetylene or diene impurities, prior to dimerisation over a solid catalyst comprising nickel oxide on a silica-alumina support, in order to suppress the normal tendency of the impurities to poison the catalyst.

According to the present invention there is provided a method of producing octenes which comprises dimerising an n-butene using a homogeneous catalyst system formed in situ from a nickel compound, an organo aluminium compound, n-butene and hydrogen.

The catalyst system is in the liquid phase and so to produce a homogeneous catalyst according to the invention gaseous hydrogen is introduced into the system in amounts sufficient to dissolve in the liquid components, preferably up to saturation. In practice of course gaseous hydrogen will also be present although it is believed that this takes no part in the catalytic action of the system, this being derived entirely from dissolved hydrogen.

Since the system is homogeneous the nickel compound and the organoaluminium compound should be miscible with the butene. Thus they may be dissolved in the butene or alternatively they may be dissolved in solvents which are inert to the reaction and which are miscible with the butene. Thus they may be dissolved in the butene or alternatively for example a paraffin such as hexane. Accordingly as nickel compound, there is preferably employed a nickel salt of a higher mono- or di-carboxylic acid, more preferably an acid having from 5 to 20 carbon atoms, such as nickel oleate, nickel dodecanoate and particularly nickel octoate. Other nickel compounds which may be mentioned are coordination complexes of organic phosphines with nickel halides, corresponding to the general formula $NiX_2.(PR_3)_2$ in which X represents chlorine, bromine or iodine and each R represents independently an alkyl or aryl group. Examples of such compounds are bis (triethyl phosphine) nickel chloride, $NiCl_2$ $(PEt_3)_2$, bis (triphenyl phosphine) nickel chloride and bis (tricyclohexyl phosphine) nickel chloride. The nickel compound can itself be soluble in the liquid butene or soluble in an inert butene compatible solvent.

Many organo aluminium compounds are suitable for use in accordance with the invention. Preferably they are alkyl aluminium compounds which contain on average from 1 to 2 alkyl groups and from 1 to 2 halogen atoms per aluminium atom. The alkyl groups preferably have up to 5 carbon atoms and are most preferably ethyl. The halogen is preferably chlorine.

Again they may themselves be soluble in liquid butene or used in a solvent which is inert to the reaction and which is compatible with liquid butene under the reaction conditions. By way of example there may be mentioned aluminium monoethyl dichloride $AtEtCl_2$, aluminium ethyl sesqui chloride and aluminium diethyl monochloride.

The temperature at which dimerisation is carried out in accordance with the invention is preferably in the range $20°$ to $70°$ C., for example from $30°$ to $50°$ C., more preferably about $40°$ C., although the actual operating temperature is dependent to an extent on the nickel and aluminium compounds employed in the catalyst system, since these may be thermally unstable.

The pressure to be employed in performing the method of the invention should be sufficient to maintain the butene in the liquid phase at the operating temperature, and is preferably in the range 2 to 20 bars abs. For example a pressure of 12 bars is required at a temperature of $40°$ C.

It has been found that the conversion of the butene to octene is dependent inter alia on the ratio of aluminium compound to nickel compound in the catalyst system. Moreover this ratio has been found to affect the distribution of the products in the product mixture. Preferably the molar ratio of aluminium compound to nickel compound in the catalyst is in the range 10:1 to 100:1, the particularly preferred value being about 25:1.

Up to a point, conversion is found to be proportional to the nickel content of the system relative to the amount of butene (containing substantially no dienes or acetylenes) subjected to the dimerisation method. Preferably the ratio of nickel (as metal, in grams) to butene (in mols) employed in the method is in the range 0.0001:1 to 0.1, more preferably 0.001:1 to 0.1:1, and particularly preferably about 0.003:1, although the actual value selected for optimum conversion depends to a great extent on the nature of the nickel compound which is used, and also on the other parameters employed.

As is mentioned hereinbefore, the requirement for the ratio of hydrogen to butene is simply that sufficient hydrogen must be used under the temperature and pressure conditions to secure dissolution in the butene. Preferably saturation is achieved, this being about 1.6 mol % hydrogen in the butene at room temperature.

The method according to the invention, which may be carried out continuously or in batch manner, has been found to be particularly useful when the n-butene feed is contaminated with isobutylene. Continuous operation of the method on contaminated feeds is of particular interest on a commerical basis.

The following Examples illustrate the invention, some being included for comparison purposes. For reasons of convenience only the batch technique is exemplified, although the continuous techniques, as well understood by those skilled in the art, are encompassed by the invention.

EXAMPLES

In each of a series of batches a 1 liter autoclave was flushed with nitrogen and then charged with 300 g of butene under conditions such that the butene was liquid. The butene feed used was varied in composition from batch to batch. Thereafter 0.3 mmole of a nickel compound and 7.5 mmol of an organo aluminium compound (AlEtCl$_2$) dissolved in hexane were added, the actual nickel compound used being nickel octoate or bis-(triethylphosphine) nickel chloride depending on the batch. These proportions correspond to an aluminium compound:nickel compound mol ratio of 25:1, and a nickel (metal):olefin ratio of 0.003:1 (g/mol). For those batches which were conducted in accordance with the invention, gaseous hydrogen was introduced into the autoclave after the butene, to a total pressure of 2 to 3 bars gauge such that the gas dissolved in the liquid butene. In each case the reaction was then allowed to proceed with stirring for 5 hours at a temperature of 42° C. The reaction was terminated by the addition of 10 ml of sulphuric acid which destroyed the catalyst system, and the product mixture was analyzed. Results are given in the following tables in which the following abbreviations and terms apply:

(i) catalyst system:
A = nickel octoate + AlEtCl$_2$
A/H$_2$ = A + hydrogen
B = NiCl$_2$ (PEt$_3$)$_2$ + AlEtCl$_2$
B/H$_2$ = B + hydrogen,
it being understood that the butene also is believed to participate in the catalyst system in some manner which has not yet been fully determined.

(ii) Butene feed:
X = 100% cis-butene-2
Y = 95 wt.% cis-butene-2 + 5 wt.% isobutene
Z = 80 wt.% cis-butene-2 + 20 wt.% isobutene (iii) Dimer composition:
indicated in wt.% of major components analysed after hydrogenation of the octene containing product mixture to the corresponding alkanes.
I = 3,4-dimethylhexane
II = 3-methylheptane
III = n-octane (iv) Average branchiness:
the average number of branches per mole of octene.

Examples 1 to 4 demonstrate the effect of including hydrogen in the catalyst system components. Thus all four Examples show products having essentially similar branchiness, saturate content (measured on the product mixture prior to hydrogenation for analysis) and dimer composition, whereas Examples 2 and 4 (in accordance with the invention) show an improved octene yield and an increased % conversion over Examples 1 and 3 (comparison).

Examples 5 to 8 show the effect of the presence in the feedstock of an impurity which is normally a catalyst poison for the method according to the invention (Examples 6 and 8) compared with the method where the catalyst contains no hydrogen (Examples 5 and 7). Thus referring to Comparison Examples 5 and 7 it may be seen that in the case of an orthodox catalyst system (without hydrogen) the presence of isobutene in the n-butene feed results in a reduced selectivity to the dimer product.

| Example | Butene Feed | Catalyst | Selectivity to dimer | Octene yield | Selectivity to trimer | Dimer Composition | | | C$^+_{13}$ | Saturate content | Average branchiness | Conversion |
|---|---|---|---|---|---|---|---|---|---|---|---|---|
| | | | | | | I | II | III | | | | |
| 1 | X | A | 88 wt.% | 60 | 14 wt.% | 22 | 67 | 11 | — | 1.0 | 1.11 | 68 |
| 2 | X | A/H$_2$ | 79 | 63 | 14 | 26 | 63.5 | 10.5 | — | 1.0 | 1.15 | 80 |
| 3 | X | B | 86 | 58.5 | 8.5 | 33 | 59 | 8 | — | 1.0 | 1.25 | 68 |
| 4 | X | B/H$_2$ | 89 | 72 | 8 | 27 | 67 | 6 | — | 0.6 | 1.21 | 81 |
| 5 | Y | B | 50 | 31.5 | 19.5 | 48 | 51 | 11 | 14.5 | 1.7 | 1.30 | 63 |
| 6 | Y | B/H$_2$ | 52.2 | 34.2 | 17.5 | 36 | 55.5 | 8.5 | 14.5 | 1.3 | 1.28 | 65.5 |
| 7 | Z | B | 49.5 | 39.6 | 19 | 40.5 | 49.5 | 10 | 15.5 | 1.3 | 1.30 | 80 |
| 8 | Z | B/H$_2$ | 64.6 | 56.8 | 15 | 36 | 57 | 7 | 13 | 1.0 | 1.34 | 88 |

In contrast, for feeds containing such impurity, Examples 6 and 8 show that the catalyst system according to the invention serves to improve the selectivity to octene (although not to the level obtainable for pure n-butene feed). This improvement is particularly marked when there is a relatively high content of isobutene (20%) in the feed. It is believed that the isobutylene reduces the effectiveness of the catalyst since it removes some of the catalytic components in a side reaction.

In general, therefore, it may be concluded from the Examples that the method according to the invention gives an improved yield and conversion of n-butene to octene, without substantial increase in the formation of saturates and without substantially changing the overall composition and branchiness of the dimer. The effect of the hydrogen is even more pronounced when the feed contains isobutylene contaminants.

I claim:

1. A method of producing octenes which comprises dimerising an n-butene using a homogeneous catalyst system formed in situ from a nickel compound, an organo aluminium compound, n-butene and hydrogen.

2. A method according to claim 1 wherein the nickel compound is soluble in the butene under dimerisation conditions.

3. A method according to claim 1 wherein the nickel compound is used in the form of a solution in an inert solvent which is miscible with the butene under dimerisation conditions.

4. A method according to claim 1, wherein the nickel compound is selected from the group consisting of salts of higher mono- and di-carboxylic acids having from 5 to 20 carbon atoms.

5. A method according to claim 4, wherein the nickel compound is nickel octoate.

6. A method according to claim 1, wherein the nickel compound is a coordination complex of an organic phosphine with a nickel halide of general formula NiX$_2$(PR$_3$)$_2$ in which x represents chlorine, bromine or iodine and each R represents an alkyl or aryl group.

7. A method according to claim 6 wherein the nickel compound is bis-(triethylphosphine) nickel chloride.

8. A method according to claim 1 wherein the organoaluminium compound is soluble in the butene under dimerisation conditions.

9. A method according to claim 1 wherein the organoaluminium compound is used in the form of a solution in an inert solvent which is miscible with the butene under dimerisation conditions.

10. A method according to claim 1 wherein the organoaluminium compound is aluminium monoethyl dichloride.

11. A method according claim 1 wherein the molar ratio of aluminium compound to nickel compound is in the range 10:1 to 100:1.

12. A method according to claim 1 wherein the ratio of nickel (as metal, in grams) to butene (in mols) is in the range 0.001:1 to 0.1:1.

13. A method according to claim 1 wherein the hydrogen is dissolved in the butene at saturation level under the dimerisation conditions.

14. A method according to claim 1 wherein the dimerisation is performed at a temperature of from 20° to 70° C.

15. A method according to claim 1 wherein the dimerisation is performed at a pressure of from 2 to 20 bars abs.

16. A method according to claim 1 wherein the n-butene used contains a contaminant such as isobutylene.

* * * * *